(12) United States Patent
Bhushan et al.

(10) Patent No.: US 9,616,008 B2
(45) Date of Patent: Apr. 11, 2017

(54) ANTIMICROBIAL COMPOSITIONS

(71) Applicants: Rajiv Bhushan, Mountain View, CA (US); Jerry Gin, Sunnyvale, CA (US); Amit Goswamy, Los Gatos, CA (US)

(72) Inventors: Rajiv Bhushan, Mountain View, CA (US); Jerry Gin, Sunnyvale, CA (US); Amit Goswamy, Los Gatos, CA (US)

(73) Assignee: LIVIONEX, Inc., Los Gatos, CA (US)

( * ) Notice: Subject to any disclaimer, the term of this patent is extended or adjusted under 35 U.S.C. 154(b) by 0 days.

(21) Appl. No.: 14/654,525

(22) PCT Filed: Dec. 20, 2013

(86) PCT No.: PCT/US2013/077332
§ 371 (c)(1),
(2) Date: Jun. 20, 2015

(87) PCT Pub. No.: WO2014/100777
PCT Pub. Date: Jun. 26, 2014

(65) Prior Publication Data
US 2015/0342848 A1    Dec. 3, 2015

Related U.S. Application Data

(60) Provisional application No. 61/740,396, filed on Dec. 20, 2012.

(51) Int. Cl.
| | | |
|---|---|---|
| A01N 25/34 | (2006.01) |
| A61K 8/46 | (2006.01) |
| A61K 8/365 | (2006.01) |
| A61K 31/194 | (2006.01) |
| A61K 8/55 | (2006.01) |
| A61K 31/6615 | (2006.01) |
| A61L 27/28 | (2006.01) |
| A61L 29/08 | (2006.01) |
| A61L 31/08 | (2006.01) |
| A61L 15/20 | (2006.01) |
| A61L 15/46 | (2006.01) |
| A61Q 19/10 | (2006.01) |
| A61K 45/06 | (2006.01) |
| A61K 31/10 | (2006.01) |
| A61K 31/198 | (2006.01) |
| A61K 9/00 | (2006.01) |
| A61K 47/18 | (2017.01) |
| A61K 47/20 | (2006.01) |
| A61L 27/54 | (2006.01) |
| A61L 29/16 | (2006.01) |
| A61L 31/16 | (2006.01) |
| A61K 8/24 | (2006.01) |
| A61K 8/44 | (2006.01) |
| A61Q 11/00 | (2006.01) |
| A61Q 15/00 | (2006.01) |
| A61Q 17/00 | (2006.01) |
| C11D 3/33 | (2006.01) |
| C11D 3/34 | (2006.01) |
| C11D 3/48 | (2006.01) |
| C11D 7/32 | (2006.01) |
| C11D 7/34 | (2006.01) |

(52) U.S. Cl.
CPC ............... *A61K 8/46* (2013.01); *A61K 8/24* (2013.01); *A61K 8/365* (2013.01); *A61K 8/44* (2013.01); *A61K 8/55* (2013.01); *A61K 9/0014* (2013.01); *A61K 31/10* (2013.01); *A61K 31/194* (2013.01); *A61K 31/198* (2013.01); *A61K 31/6615* (2013.01); *A61K 45/06* (2013.01); *A61K 47/183* (2013.01); *A61K 47/20* (2013.01); *A61L 15/20* (2013.01); *A61L 15/46* (2013.01); *A61L 27/28* (2013.01); *A61L 27/54* (2013.01); *A61L 29/08* (2013.01); *A61L 29/16* (2013.01); *A61L 31/08* (2013.01); *A61L 31/16* (2013.01); *A61Q 11/00* (2013.01); *A61Q 15/00* (2013.01); *A61Q 17/005* (2013.01); *A61Q 19/10* (2013.01); *C11D 3/33* (2013.01); *C11D 3/3454* (2013.01); *C11D 3/48* (2013.01); *C11D 7/3245* (2013.01); *C11D 7/34* (2013.01); *A61K 2800/51* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 5,817,630 A | 10/1998 | Hofmann | |
| 2004/0137068 A1 | 7/2004 | Bhushan et al. | |
| 2004/0192647 A1 | 9/2004 | Babizhayev | |
| 2006/0134020 A1* | 6/2006 | Robinson | A61K 8/0216 424/52 |
| 2006/0166879 A1 | 7/2006 | Bhushan et al. | |
| 2007/0021505 A1 | 1/2007 | Bhushan et al. | |
| 2008/0038219 A1 | 2/2008 | Mosbaugh et al. | |
| 2010/0035992 A1* | 2/2010 | Bhushan | A61K 31/10 514/566 |
| 2010/0063152 A1 | 3/2010 | Bhushan et al. | |
| 2010/0086495 A1 | 4/2010 | Rubinstein | |
| 2010/0209419 A1 | 8/2010 | Bhushan et al. | |
| 2015/0132347 A1 | 5/2015 | Bhushan et al. | |

FOREIGN PATENT DOCUMENTS

| | | |
|---|---|---|
| WO | 0215860 A1 | 2/2002 |
| WO | 2009046116 A1 | 4/2009 |
| WO | 2009063522 A1 | 5/2009 |

OTHER PUBLICATIONS

Bates et al. (WO 2008/092011 A2).*
* cited by examiner

*Primary Examiner* — Robert A Wax
*Assistant Examiner* — Quanglong Truong
(74) *Attorney, Agent, or Firm* — Shantanu Basu; Eckman Basu LLP

(57) ABSTRACT

An anti-microbial composition, comprising a chelator (such as EDTA and its salts), and a transport enhancer (such as Methyl Sufonyl Methane; MSM) is provided. Together, the combination of the two substances unexpectedly and beneficially inhibits bacterial or fungal biofilms when administered to an area of microbial infection. Preferred formulations include spray, lotion, solution, gel, cream, ointment, soap, deodorant, surgical rinse, or dental rinse.

20 Claims, 1 Drawing Sheet

1A
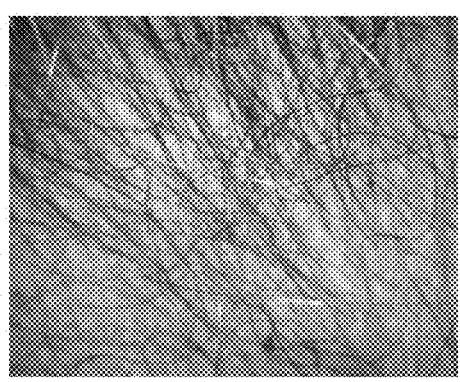
1B

ANTIMICROBIAL COMPOSITIONS

CROSS-REFERENCE TO RELATED APPLICATIONS

This application is a 371 National Stage filing of international application filed under the Paris Convention Treaty (PCT) No. PCT/US2013/077332 filed Dec. 20, 2013 which claims priority to U.S. Provisional Patent Application Ser. No. 61/740,396 filed Dec. 20, 2012 and titled ANTIMICROBIAL COMPOSITIONS, the contents of which are incorporated herein in their entirety.

TECHNICAL FIELD OF THE INVENTION

This invention relates generally to the field of antimicrobial compositions. More particularly, it relates to antimicrobial agents and methods of eliminating biofilm and planktonic cells using these antimicrobial agents. In particular, the invention relates to antimicrobial compositions containing a transport enhancer and a chelating agent. In one exemplary embodiment, it relates to such compositions which contain MSM and EDTA.

BACKGROUND OF THE INVENTION

It is believed that all wounds are colonized by microbes. If the microbes reach a level of clinical infection, their presence is believed to impair healing and may be a contributing factor to wound chronicity. It has recently been estimated that hospital-acquired (nosocomial) infections are the fourth-leading cause of death in the United States, affecting 2 million patients per year and causing over 100,000 annual deaths, with a total annual cost of over $30 billion. *Staphylococcal* species such as *S. epidermidis* and *S. aureus* are responsible for the majority of nosocomial infections; treatment of these infections is often made much more challenging by the tendency of staphylococci to form biofilms.

Recently researchers have proposed that it may not be planktonic but rather biofilm communities which contribute to wound chronicity. Biofilms are polymicrobial groupings of bacteria which are held together in an extracellular polymeric substance consisting of protein, DNA, and polysaccarhides and are not totally susceptible to antibiotic treatment. It has been shown that 60% of the chronic wounds tested contained biofilm. (James et al., Wound Repair Regen., 16(1):37-44, 2008.)

Biofilms are populations of bacteria or fungi growing attached to an inert or living surface. Mounting evidence has shown that biofilms constitute a significant threat to human health. The Public Health Service estimates that biofilms are responsible for more than 80% of bacterial infections in humans (National Institutes of Health, 1998 RFA#DE-98-006). Examples of diseases caused by biofilms include dental caries, periodontitis, cystic fibrosis pneumonia, native valve endocarditis, and otitis media (Costerton et al. *Science* 1999 284:1318-1322), as well as infection of various medical devices such as urinary catheters, mechanical heart valves, cardiac pacemakers, prosthetic joints, and contact lenses (Donlan, R. M. 2001 *Emerging Infect. Dis.* 7:277-281). Fungi also form biofilms of clinical significance, for example *Candida* infections. Biofilm infections afflict tens of millions of patients in the U.S. annually and require a significant expenditure of health care dollars (Costerton et al. *Science* 1999 284:1318-1322). Bacteria growing in biofilms exhibit increased resistance to antimicrobial agents and are nearly impossible to eradicate. New methods for treating biofilm infections are needed.

Bacterial biofilms are sources of contamination that are difficult to eliminate in a variety of industrial, environmental and clinical settings. Biofilms are polymer structures secreted by bacteria to protect bacteria from various environmental attacks, and thus result also in protection of the bacteria from disinfectants and antibiotics. Biofilms may be found on any environmental surface where sufficient moisture and nutrients are present. Bacterial biofilms are associated with many human and animal health and environmental problems. For instance, bacteria form biofilms on implanted medical devices, e.g., catheters, heart valves, joint replacements, and damaged tissue, such as the lungs of cystic fibrosis patients. Biofilms also contaminate surfaces such as water pipes and the like, and render also other industrial surfaces hard to disinfect.

Biofilm is commonly known as the primary cause of many diseases and infections in biology. Biofilms also play a detrimental role on many other non biological surfaces. These biofilms, which exists not only on biological surfaces but also on all manner of surfaces, can be defined as a diverse community of microorganisms. The microorganisms bind tightly to one another, in addition to the solid surface, by means of an extracellular matrix consisting of polymers of both host and microbial origin.

Biofilms, exhibit an open architecture. The open architecture, which consists of channels and voids, helps to achieve the flow of nutrients, waste products, metabolites, enzymes, and oxygen through the biofilm. Because of this structure, a variety of microbial organisms can make up biofilms, including both aerobic and anaerobic bacteria. The microbial composition of biofilms includes a multitude of species of bacteria, archaea, fungi and viruses, which all exist in a relatively stable environment called microbial homeostasis. Biofilms are responsible for many of the diseases common in the body including dental diseases, non healing wounds and sores. Biofilms also are the cause of undesirable body odor resulting from biofilms on the body surfaces. Further biofilms are common on many engineering surfaces, and lead to material erosion, and to subpar engineering performance of these surfaces.

Bacterial biofilms are ubiquitous in nature and are usually defined as matrix-enclosed bacterial populations which adhere to each other and/or to surfaces or interfaces. Bacterial biofilm formation is an extremely common phenomenon with a major economic impact in different industrial, medical and environmental fields. Biofilms can comprise a single species or multiple species and can form on a wide range of abiotic and biotic surfaces and interfaces. Although polymicrobial biofilms predominate in most situations single species biofilms can occur under certain circumstances and are an increasing problem on the surface of medical implants. Growth as a biofilm offers a number of significant advantages to the bacterium over planktonic growth not the least of which is the attachment to the surface that enables the bacterium to localize itself in a favorable environment. In polymicrobial biofilms metabolic activities can be integrated and the presence of a variety of species allows for greater flexibility in metabolic and catabolic activities as the 'genome' of the biofilm population increases with increasing species diversity. The Centers for. Disease Control and Prevention estimate that 65% of human bacterial infections involve biofilms. Biofilms often complicate treatment of chronic infections by protecting bacteria from the immune system, decreasing antibiotic efficacy and dispersing planktonic cells to distant sites that can promote re-infection. Bacterial cells within a biofilm have been shown to be up to 500 times more resistant to certain antimicrobial agents than planktonic cells which is achieved by a number of processes including, the slowing of penetration of some antimicrobial agents into the biofilm matrix, the slowing of the growth rate of bacteria in the deeper layers of the biofilm and the binding of some antimicrobial agents to extracellular polymers thereby reducing the effective concentration. In addition, microbial biofilms have been described as microbial landscapes, which have a topography that protects against shear stress whilst allowing mass transfer. Most importantly in the oral cavity failure to attach and grow as a biofilm will rapidly result in clearance.

The oral cavity is a fertile environment for the growth of bacteria with a range of hard and soft tissue surfaces that provide a variety of distinctly different microhabitats. The stability of oral microbial biofilms requires dynamic balances by a range of synergistic and antagonistic interactions among species and the environment they create. Minor adjustments in the oral environment can affect these natural balances potentially leading to shifts in the ecology and changes in the species composition of oral microbial biofilms. For example, increased dental caries incidence is often caused by increased consumption of dietary carbohydrates, which is linked to the acidification of fluids at the tooth surface due to the bacterial fermentation of these carbohydrates. Experts agree that most forms of periodontal disease are caused by specific pathogens, particularly gram-negative bacteria. The microbial composition of dental biofilms includes over 700 species of bacteria and archaea, which all exist in a relatively stable environment called microbial homeostasis. (Kroes I, Lepp P W, Reiman D A Bacterial diversity within the human subgingival crevice. *Proc Natl Acad Sci USA* 1999; 96(25):14547-14552.)

Bacterial biofilms develop in variety of bodily cavities, including those of the ear, such as the middle ear, and of the nose, such as the frontal or maxillary sinuses, for example. Once bacterial growth has been established, the bacteria will often aggregate, stop dividing, and begin forming protective bacterial biofilm layers, or "slime layers," comprised of polysaccharide matrices.

The protective bacterial biofilm interferes with the body's natural immune response as well as traditional methods of treatment. In particular, the bacteria emit exotoxins, which incite the body's immune system to respond with white cells. However, the bacterial biofilm interferes with the efficacy of the white cells' ability to attack the bacteria. The biofilm can also act as a barrier against topical administration of antibiotics and other medicaments.

Biofilm-forming bacteria also present obstacles to traditional, antibiotic treatments that act to kill dividing bacteria. In particular, the bacteria in a biofilm-forming state may have already ceased cell division, rendering such antibiotics largely ineffective. Antibiotic doses that kill free-floating bacteria, for example, need to be increased as much as 1,500 times to kill biofilm bacteria. At these high doses, the antibiotic is more likely to kill the patient before the biofilm bacteria. (Elder M J, at al. Biofilm-related infections in ophthalmology. *Eye* 1995; vol. 9 (Pt. 1):102-109.)

Methods of inhibiting biofilm formation in medical and industrial settings have previously been developed using metal chelators, specifically iron chelators. For example, U.S. Pat. No. 6,267,979, issued Jul. 31, 2001, to Raad et al., discloses the use of metal chelators in combination with antifungal or antibiotic compositions for the prevention of biofouling in water treatment, pulp and paper manufacturing and oil field water flooding. U.S. Pat. No. 7,314,857, issued Jan. 1, 2008, to Madhyastha, discloses synergistic antimicrobial compositions for inhibiting biofilm formation using combinations of an iron-sequestering glycoprotein, a cationic peptide, and an iron chelating agent. U.S. Pat. No. 7,446,089, issued Nov. 4, 2008, to Singh et al., is also directed to methods of inhibiting biofilm formation by limiting the amount of iron available to a population of bacteria, such that biofilm formation can be inhibited. These disclosures generally target iron, a higher affinity metal ion.

Given the serious medical, industrial, and environmental problems associated with bacterial biofilms, the need persists to develop targeted approaches to inhibit biofilm formation. Therefore, there it is desirable to develop an agent that efficiently controls and inhibits biofilm formation in medical and industrial applications.

SUMMARY OF THE INVENTION

MSM and EDTA (chelators in general) were not known to have an antimicrobial effect. MSM also does not have any anti-microbial properties. However, treatment with a combination of a transport enhancer (e.g., MSM) and chelator (e.g., EDTA) surprisingly and unexpectedly showed dramatic reductions in levels of bacteria and fungi.

In some embodiments, the present invention relates to methods for use of the formulations comprising a transport enhancer (such as MSM) and a chelating agent (EDTA) for reduction of microbial levels on a surface.

In particular embodiments, the chelating agents are selected from the tetrasodium salt of iminodisuccinic acid (Baypure® CX100; LANXESS GMBH (previously Bayer Chemicals) Leverkusen, DE) or salts of poly-aspartic acid (Baypure® DS100; LANXESS GMBH, Leverkusen, DE).

In some embodiments, the chelating agents are tetra sodium salts of L-glutamic acid N,N-diacetic acid (GLDA-Dissolvine®, AkzoNobel, Netherlands).

In one aspect of the invention, methods are provided for prevention or treatment of dental plaque or calculus in a subject.

The method involves administering to the subject an effective amount of a formulation composed of a therapeutically effective amount of a chelating agent and an effective transport-enhancing amount of a transport enhancer having the formula (I)

wherein $R^1$ and $R^2$ are independently selected from $C_2$-$C_6$ alkyl, $C_1$-$C_6$ heteroalkyl, $C_6$-$C_{14}$ aralkyl, and $C_2$-$C_{12}$ heteroaralkyl, any of which may be substituted, and Q is S or P.

The transport enhancing agent can be, for example, methylsulfonylmethane (MSM; also referred to as methylsulfone, dimethylsulfone, and $DMSO_2$), and the chelating agent can be ethylene diamine tetra-acetic acid (EDTA) and the like.

The formulation may be administered in any form suitable including liquid, paste, gel, solid and particulate solid state compositions. Additionally, in a preferred embodiment, the formulation is entirely composed of components that are naturally occurring and/or as GRAS ("Generally Regarded as Safe") by the U.S. Food and Drug Administration.

Accordingly, the present invention provides a method for inhibiting formation of a biofilm comprising bacteria, the method comprising contacting the bacteria with an effective amount of a formulation comprising a transport enhancer (such as MSM) and a chelating agent (such as EDTA), whereby formation of the biofilm is inhibited.

In another embodiment, the present invention provides a method for inhibiting formation of a biofilm on a device, the method comprising contacting the bacteria with an effective amount of a formulation comprising a transport enhancer (such as MSM) and a chelating agent (such as EDTA), whereby formation of a biofilm on the device is inhibited.

In another embodiment, the present invention provides a topical pharmaceutical composition for inhibiting formation of a biofilm on or within a mammal, comprising an effective amount of a formulation comprising a transport enhancer (such as MSM) and a chelating agent (such as EDTA), and at least one pharmaceutically acceptable carrier.

In a further embodiment, the present invention provides a surgical rinse for inhibiting formation of a biofilm comprising bacteria, wherein the surgical rinse comprises an effective amount of a formulation comprising a transport enhancer (such as MSM) and a chelating agent (such as EDTA).

In yet another embodiment, the present invention provides a method for inhibiting formation of a biofilm comprising bacteria, the method comprising contacting the bacteria with an effective amount of a formulation comprising a transport enhancer (such as MSM) and a chelating agent (such as EDTA), wherein the bacteria are selected from the group consisting of *Acidothennus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtheriae, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Fingoldia magna, Geobacillus kaustophilus, Geobacillus thermodenitrificans, Janibacter* sp., *Kineococcus radiotolerans, Lactobacillus fennentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides* sp., *Nocardia farcinica, Oceanobacillus iheyensis, Pelotomaculum thermopropionicum, Rhodococcus* sp., *Saccharopolyspora erythraea*, coagulase-negative *Staphylococcus* species, *Staphylococcus aureus*, methicillin resistant *Staphylococcus aureus* (MRSA), *Staphylococcus epidermidis*, methicillin resistant *Staphylococcus epidermidis* (MRSE), *Streptococcus agalactiae, Streptococcus gordonii, Streptococcus mitis, Streptococcus oxalis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis,* and combinations thereof, whereby formation of the biofilm is inhibited.

A further embodiment of the present invention provides a bandage impregnated with a safe and effective amount of a formulation comprising a transport enhancer (such as MSM) and a chelating agent (such as EDTA), wherein the bandage inhibits the formation of a biofilm on the skin.

Yet another embodiment of the present invention provides a personal cleansing formulation comprising a transport enhancer (such as MSM) and a chelating agent (such as EDTA), wherein the personal cleansing composition inhibits formation of a biofilm on the skin.

A further embodiment of the present invention provides a hard surface cleaning formulation comprising a transport enhancer (such as MSM) and a chelating agent (such as EDTA), wherein the composition inhibits formation of a biofilm on a hard surface.

A further embodiment of the present invention provides a dental rinse for inhibiting formation of a biofilm, the dental rinse comprising a formulation comprising a transport enhancer (such as MSM) and a chelating agent (such as EDTA).

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 1a shows *Trichmichosis axillaris* in the armpit of a human subject. FIG. 1b shows complete resolution of *Trichmichosis axillaris* in the armpit of the subject following treatment in about 48 hours.

DETAILED DESCRIPTION OF THE INVENTION

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Throughout this application, various publications, patents and published patent applications are cited. The inventions of these publications, patents and published patent applications referenced in this application are hereby incorporated by reference in their entireties into the present invention. Citation herein of a publication, patent, or published patent application is not an admission the publication, patent, or published patent application is prior art.

As used herein and in the appended claims, the singular forms "a," "and," and "the" include plural referents unless the context clearly dictates otherwise. Thus, for example, "a transport enhancer" encompasses a plurality of transport enhancers as well as a single transport enhancer. Reference to "a chelating agent" includes reference to two or more chelating agents as well as a single chelating agent, and so forth. In this specification and in the claims that follow, reference will be made to a number of terms, which shall be defined to have the following meanings:

When referring to a formulation component, it is intended that the term used, e.g., "agent," encompass not only the specified molecular entity but also its pharmaceutically acceptable analogs, including, but not limited to, salts, esters, amides, prodrugs, conjugates, active metabolites, and other such derivatives, analogs, and related compounds.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. Unless otherwise indicated herein, either explicitly or by implication, if the term "treatment" (or "treating") is used without reference to possible prevention, it is intended that prevention be encompassed as well, such that "a method for the treatment of gingivitis" would be interpreted as encompassing "a method for the prevention of gingivitis."

"Optional" or "optionally present"—as in an "optional substituent" or an "optionally present additive" means that the subsequently described component (e.g., substituent or additive) may or may not be present, so that the description includes instances where the component is present and instances where it is not.

By "pharmaceutically acceptable" is meant a material that is not biologically or otherwise undesirable, e.g., the material may be incorporated into a formulation of the invention without causing any undesirable biological effects or interacting in a deleterious manner with any of the other components of the dosage form formulation. However, when the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration. As explained in further detail infra, "pharmacologically active" (or simply "active") as in a "pharmacologically active" derivative or analog refers to derivative or analog having the same type of pharmacological activity as the parent agent. The terms "treating" and "treatment" as used herein refer to reduction in severity and/or frequency of symptoms, elimination of symptoms and/or underlying cause, prevention of the occurrence of symptoms and/or their underlying cause, and improvement or remediation of an undesirable condition or damage. Thus, for example, "treating" a subject involves prevention of an adverse condition in a susceptible individual as well as treatment of a clinically symptomatic individual by inhibiting or causing regression of the condition. The term "chelating agent" (or "active agent") refers to any chemical compound, complex or composition that exhibits a desirable effect in the biological context, i.e., when administered to a subject or introduced into cells or tissues in vitro. The term includes pharmaceutically acceptable derivatives of those active agents specifically mentioned herein, including, but not limited to, salts, esters, amides, prodrugs, active metabolites, isomers, analogs, crystalline forms, hydrates, and the like. When the term "chelating agent" is used, or when a particular chelating agent is specifically identified, it is to be understood that pharmaceutically acceptable salts, esters, amides, prodrugs, active metabolites, isomers, analogs, etc. of the agent are intended as well as the agent per se.

By an "effective" amount or a "therapeutically effective" amount of an active agent is meant a nontoxic but sufficient amount of the agent to provide a beneficial effect. The amount of active agent that is "effective" will vary from subject to subject, depending on the age and general condition of the individual, the particular active agent or agents, and the like. Unless otherwise indicated, the term "therapeutically effective" amount as used herein is intended to encompass an amount effective for the prevention of an adverse condition and/or the amelioration of an adverse condition, i.e., in addition to an amount effective for the treatment of an adverse condition.

As will be apparent to those of skill in the art upon reading this invention, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

Unless otherwise indicated, the invention is not limited to specific formulation components, modes of administration, chelating agents, manufacturing processes, or the like, as such may vary.

Unless otherwise defined, all technical and scientific terms used herein have the same meaning as commonly understood by one of ordinary skill in the art to which this invention pertains. In the case of conflict, the present document, including definitions will control.

DEFINITIONS

The term "biofilm" refers to matrix-enclosed microbial accretions to biological or non-biological surfaces. Biofilm formation represents a protected mode of growth that allows cells to survive in hostile environments.

The term "biofilm formation" is intended to include the formation, growth, and modification of the bacterial colonies contained with biofilm structures, as well as the synthesis and maintenance of the polysaccharide matrix of the biofilm structures.

The term "gram positive bacteria" refers to bacteria having cell walls with high amounts of peptidoglycan. Gram positive bacteria are identified by their tendency to retain crystal violet and stain dark blue or violet in the Gram staining protocol.

The term "gram negative bacteria" refers to bacteria having thinner peptidoglycan layers which do not retain the crystal violet stain in the Gram staining protocol and instead retain the counterstain, typically safranin. Gram negative bacteria stain red or pink in the Gram staining protocol.

The term "antimicrobial agent" refers to any substance that kills or prevents the growth of bacteria or other microbes.

A non-limiting list of bacteria that may be susceptible to the antimicrobial compositions of the invention include: *Acidothennus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtheriae, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Fingoldia magna, Geobacillus kaustophilus, Geobacillus thermodenitrificans, Janibacter sp., Kineococcus radiotolerans, Lactobacillus fennentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides sp., Nocardia farcinica, Oceanobacillus iheyensis, Pelotomaculum thermopropionicum, Rhodococcus sp., Saccharopolyspora erythraea,* coagulase-negative *Staphylococcus* species, *Staphylococcus aureus,* methicillin resistant *Staphylococcus aureus* (MRSA), *Staphylococcus epidermidis,* methicillin resistant *Staphylococcus epidermidis* (MRSE), *Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis,* and combinations thereof.

The term "antibiotic" refers to a substance that is antagonistic to the growth of microorganisms. Suitable antibiotics may be naturally-occurring, chemically-modified, or synthetically-produced.

The term "surgical rinse" refers to a solution used during surgery to irrigate the site of an implanted medical device, with the intent to prevent initial formation of biofilms in the vicinity of the medical device.

The term "dental rinse" refers to a solution containing one or more zinc chelators used as a mouthwash or rinse to prevent the establishment of oral biofilms that lead to dental caries.

The term "personal cleansing composition" refers to a composition that is used for personal hygiene. Personal cleansing compositions include, but are not limited to: gels, creams, suspensions, colloids, soaps, deodorants, body washes, shampoos, and the like. In one embodiment, the personal cleansing compositions of the present invention inhibit biofilm-related infections including, but not limited to, community-acquired methicillin-resistant *Staphylococcus aureus* (CA-MRSA) infection.

The term "hard surface cleaning composition" refers to a composition that is used to clean and/or sanitize a hard or solid surface. In one embodiment, the invention provides a composition that prevents bacterial biofilm growth on hard surfaces including, but not limited to, surgical instruments, storage tanks, pipelines, trays, containers, walls, floors, countertops, locker room floors, benches, lockers, showers, bathrooms, toilets, water filtration units, and the like.

Chelating agent: Chelation is a chemical combination with a metal in complexes in which the metal is part of a ring. An organic ligand is called a chelator or chelating agent, the chelate is a metal complex. The larger number of ring closures to a metal atom the more stable is the compound. The stability of a chelate is also related to the number of atoms in the chelate ring. Monodentate ligands which have one coordinating atom like $H_2O$ or $NH_3$ are easily broken apart by other chemical processes, whereas polydentate chelators, donating multiple binds to metal ion, provide more stable complexes. Chlorophyll, a green plant pigment, is a chelate that consists of a central magnesium atom joined with four complex chelating agent (pyrrole ring). Heme is an iron chelate which contains iron (II) ion in the center of the porphyrin. Chelating agents offers a wide range of sequestrants to control metal ions in aqueous systems. By forming stable water soluble complexes with multivalent metal ions, chelating agents prevent undesired interaction by blocking normal reactivity of metal ions. EDTA (ethylenediamine tetraacetate) is a good example of common chelating agents which have nitrogen atoms and short chain carboxylic groups.

Examples of chelators of iron and calcium include, but are not limited to, Diethylene triamine pentaacetic acid (DTPA), ethylene diamine tetraacetic acid (EDTA), nitrilotriacetic acid (NTA), 1,3-propylene diamine tetraacetic acid (PDTA), Ethylene diamine disuccinic acid (EDDS), and ethylene glycol tetraacetic acid (EGTA). Any suitable chelating agent known in the art, which is biologically safe and able to chelate iron, calcium or other metals, is suitable for the invention.

Compounds useful as chelating agents herein include any compounds that coordinate to or form complexes with a divalent or polyvalent metal cation, thus serving as a sequestrant of such cations. Accordingly, the term "chelating agent" herein includes not only divalent and polyvalent ligands (which are typically referred to as "chelators") but also monovalent ligands capable of coordinating to or forming complexes with the metal cation.

Suitable biocompatible chelating agents useful in conjunction with the present invention include, without limitation, monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ATPA), citric acid, pharmaceutically acceptable salts thereof, and combinations of any of the foregoing. Other exemplary chelating agents include: phosphates, e.g., pyrophosphates, tripolyphosphates, and hexametaphosphates.

EDTA and ophthalmologically acceptable EDTA salts are particularly preferred, wherein representative ophthalmologically acceptable EDTA salts are typically selected from diammonium EDTA, disodium EDTA, dipotassium EDTA, triammonium EDTA, trisodium EDTA, tripotassium EDTA, and calcium disodium EDTA.

EDTA has been widely used as an agent for chelating metals in biological tissue and blood, and has been suggested for inclusion in various formulations. For example, U.S. Pat. No. 6,348,508 to Denick Jr. et al. describes EDTA as a sequestering agent to bind metal ions. In addition to its use as a chelating agent, EDTA has also been widely used as a preservative in place of benzalkonium chloride, as described, for example, in U.S. Pat. No. 6,211,238 to Castillo et al. U.S. Pat. No. 6,265,444 to Bowman et al. discloses use of EDTA as a preservative and stabilizer. However, EDTA has generally not been applied topically in any significant concentration formulations because of its poor penetration across biological membranes and biofilms including skin, cell membranes and even biofilms like dental plaque.

Among the chelating/sequetering materials which may be included in the compositions there may be mentioned biocompatible chelating agents include, without limitation, monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ATPA), citric acid, pharmaceutically acceptable salts thereof, and combinations of any of the foregoing.

Other exemplary chelating agents include: phosphates, e.g., pyrophosphates, tripolyphosphates, and hexametaphosphates. Other exemplary chelating agents include: phosphates, e.g., pyrophosphates, tripolyphosphates, and hexametaphosphates; chelating antibiotics such as chloroquine and tetracycline; nitrogen-containing chelating agents containing two or more chelating nitrogen atoms within an imino group or in an aromatic ring (e.g., diimines, 2,2'-bipyridines, etc.); and polyamines such as cyclam (1,4,7,11-tetraazacyclotetradecane), N—($C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), deferoxamine (N'-{5-[Acetyl(hydroxy)amino]pentyl}-N-[5-({4-[(5-aminopentyl)(hydroxy)amino]-4-oxobutanoyl}amino) pentyl]-N-hydroxysuccinamide, or N'-[5-(Acetyl-hydroxyamino)pentyl]-N-[5-[3-(5-aminopentyl-hydroxycarbamoyl) propanoylamino]pentyl]-N-hydroxy-butane diamide); also known as desferrioxamine B, desferoxamine B, DFO-B, DFOA, DFB or desferal), deferiprone, pyridoxal isonicotinoyl hydrazone (PIH), salicylaldehyde isonicotinoyl hydrazone (SIH), ethane-1,2-bis(N-1-amino-3-ethylbutyl-3-thiol).

Additional, suitable biocompatible chelating agents which may be useful for the practice of the current disclosure include EDTA-4-aminoquinoline conjugates such as ([2-(Bis-ethoxycarbonylmethyl-amino)-ethyl]-{[2-(7-chloro-quinolin-4-ylamino)-ethylcarbamoyl]-methyl}-amino)-acetic acid ethyl ester, ([2-(Bis-ethoxycarbonylmethyl-amino)-propyl]-{[2-(7-chloro-quinolin-4-ylamino)-ethylcarbamoyl]-methyl}-amino)-acetic acid ethyl ester, ([3-(Bis-ethoxycarbonylmethyl-amino)-propyl]-{[2-(7-chloro-quinolin-4-ylamino)-ethylcarbamoyl]-methyl}-amino)-acetic acid ethyl ester, ([4-(Bis-ethoxycarbonylmethyl-amino)-butyl]-{[2-(7-chloro-quinolin-4-ylamino)-ethylcarbamoyl]-methyl}-amino)-acetic acid ethyl ester, ([2-(Bis-ethoxymethyl-amino)-ethyl]-{[2-(7-chloro-quinolin-4-ylamino)-ethylcarbamoyl]-methyl}-amino)-acetic acid ethyl ester, ([2-(Bis-ethoxymethyl-amino)-propyl]-{[2-(7-chloro-quinolin-4-ylamino)-ethylcarbamoyl]-methyl}-amino)-acetic acid ethyl ester, ([3-(Bis-ethoxymethyl-amino)-propyl]-{[2-(7-chloro-quinolin-4-ylamino)-ethylcarbamoyl]-methyl}-amino)-acetic acid ethyl ester, ([4-(Bis-ethoxymethyl-amino)-butyl]-{[2-(7-chloro-quinolin-4-ylamino)-ethylcarbamoyl]-methyl}-amino)-acetic acid ethyl ester as described in Solomon et al., *Med. Chem.* 2: 133-138, 2006.

Additionally, natural chelators including, but not limited to citric acid, phytic acid, lactic acid, acetic acid and their salts. Other natural chelators and weak chelators include but are not limited to curcumin (turmeric), ascorbic acid, succinic acid, and the like.

In some embodiments, the chelating agents are selected from the tetrasodium salt of iminodisuccinic acid (Baypure® CX100; LANXESS GMBH (previously Bayer Chemicals) Leverkusen, DE) or salts of poly-aspartic acid (Baypure® DS100; LANXESS GMBH, Leverkusen, DE). In some embodiments, the chelating agents are tetra sodium salts of L-glutamic acid N,N-diacetic acid (GLDA—Dissolvine®, AkzoNobel, Netherlands).

In some embodiments, the chelating agent incorporated in the formulation is a prochelator. A prochelator is any molecule that is converted to a chelator when exposed to the appropriate chemical or physical conditions. For example, BSIH (isonicotinic acid [2-(4,4,5,5-tetramethyl-[1,3,2]dioxaborolan-2-yl)-benzylidene]-hydrazide) prochelators are converted by hydrogen peroxide into SIH (salicylaldehyde isonicotinoyl hydrazone) iron-chelating agents that inhibit iron-catalyzed hydroxyl radical generation.

The inactivated metal ion sequestering agent is sometimes referred to herein as a "prochelator," although sequestration of metal ions can involve sequestration and complexation processes beyond the scope of chelation per se. The term "prochelator" is analogous to the term "prodrug" insofar as a prodrug is a therapeutically inactive agent until activated in vivo, and the prochelator, as well, is incapable of sequestering metal ions until activated in vivo.

Transport Enhancer: The transport enhancer is selected to facilitate the transport of a chelating agent through the tissues, extra-cellular matrices, and/or cell membranes of a body. An "effective amount" of the transport enhancer represents an amount and concentration within a formulation of the invention that is sufficient to provide a measurable increase in the penetration of a chelating agent through one or more of the sites of oral cavity or teeth in a subject than would otherwise be the case without the inclusion of the transport enhancer within the formulation.

In certain instances, the transport enhancer may be present in a formulation of the invention in an amount that ranges from about 0.01 wt. % or less to about 30 wt. % or more, typically in the range of about 0.1 wt. % to about 20 wt. %, more typically in the range of about 1 wt. % to about 11 wt. %, and most typically in the range of about 2 wt. % to about 8 wt. %, for instance, 5 wt. %.

The transport enhancer is generally of the formula (I)

wherein $R^1$ and $R^2$ are independently selected from $C_2$-$C_6$ alkyl, $C_1$-$C_6$ heteroalkyl, $C_6$-$C_{14}$ aralkyl, and $C_2$-$C_{12}$ heteroaralkyl, any of which may be substituted, and Q is S or P. Compounds wherein Q is S and $R^1$ and $R^2$ are $C_1$-$C_3$ alkyl are preferred, with methylsulfonylmethane (MSM) being the optimal transport enhancer.

The phrase "having the formula" or "having the structure" is not intended to be limiting and is used in the same way that the term "comprising" is commonly used. With respect to the above structure, the term "alkyl" refers to a linear, branched, or cyclic saturated hydrocarbon group containing 1 to 6 carbon atoms, such as methyl, ethyl, n-propyl, isopropyl, n-butyl, isobutyl, t-butyl, cyclopentyl, cyclohexyl and the like. If not otherwise indicated, the term "alkyl" includes unsubstituted and substituted alkyl, wherein the substituents may be, for example, halo, hydroxyl, sulfhydryl, alkoxy, acyl, etc. The term "alkoxy" intends an alkyl group bound through a single, terminal ether linkage; that is, an "alkoxy" group may be represented as —O-alkyl where alkyl is as defined above. The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 14 carbon atoms. Exemplary aryl groups are contain one aromatic ring or two fused or linked aromatic rings, e.g., phenyl, naphthyl, biphenyl, diphenylether, diphenylamine, benzophenone, and the like. "Aryl" includes unsubstituted and substituted aryl, wherein the substituents may be as set forth above with respect to optionally substituted "alkyl" groups. The term "aralkyl" refers to an alkyl group with an aryl substituent, wherein "aryl" and "alkyl" are as defined above. Preferred aralkyl groups contain 6 to 14 carbon atoms, and particularly preferred aralkyl groups contain 6 to 8 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The term "acyl" refers to substituents having the formula —(CO)-alkyl, —(CO)-aryl, or —(CO)-aralkyl, wherein "alkyl," "aryl, and "aralkyl" are as defined above. The terms "heteroalkyl" and "heteroaralkyl" are used to refer to heteroatom-containing alkyl and aralkyl groups, respectively, i.e., alkyl and aralkyl groups in which one or more carbon atoms is replaced with an atom other than carbon, e.g., nitrogen, oxygen, sulfur, phosphorus or silicon, typically nitrogen, oxygen or sulfur.

The term "implantable medical device" refers to any medical device implanted or inserted in the human body. Such devices can be temporarily or permanently implanted or inserted. An implantable medical device can be, for example, catheters, orthopedic devices, prosthetic devices, vascular stents, urinary stents, pacemakers, implants, or the like.

The term "bathing a device" refers to submerging a device in a solution in order to pre-treat the device, for example, prior to surgical implantation. Bathing a device can also occur after the device has been surgically implanted, for example, by irrigating the surgical site with a sterile solution.

The term "coating a device" refers to pre-treating a device with a composition prior to surgical implantation. Suitable compositions for pre-treating the device may include, for example, solutions, gels, polymer coatings, and the like. A variety of means may be employed to coat a device, such as spraying or submerging the device. The coated device comprises a surface layer having desirable properties conferred by the coating composition. In one embodiment, the coating composition comprises at least one zinc chelator. In another embodiment, the coating composition comprises one or more soluble G5 domains or zinc adhesion modules.

The term "topical pharmaceutical composition" refers to pharmaceutical compositions suitable for dermal administration to a mammal. Suitable topical pharmaceutical compositions include, but are not limited to, gels, creams, lotions, ointments, tinctures, sprays, and solids. In one embodiment, a topical pharmaceutical composition of the present invention is applied on the outer surface of the skin or in the vicinity of cuts, abrasions, turf burn injuries, lacerations, burns, or puncture wounds in order to treat, prevent, or inhibit the formation of bacterial biofilms.

Biofilms

Biofilms are bacterial communities that adhere to biological or abiotic substrata, differentiate into micro- and macrocolonies, and produce an extracellular matrix typically comprised of polysaccharides and proteins. Bacteria in biofilms are resistant to antibiotics and host immune responses and are extremely difficult to eradicate. For example, device-related infections due to *staphylococcal* biofilms often require surgical removal of the implanted device, debridement of the surrounding tissue, and prolonged antibiotic treatment.

The formation of biofilms includes a series of steps that begins with the initial colonization of the surface and ends with the complex formation of a mature biofilm. Biofilms exist on a variety of surfaces including tissues, smooth surfaces and biological crevices, however they are most likely to be seen in their mature state in the more stagnant sites, like fissures and crevices, as these places provide protection from the forces of removal, like fluid flow and mechanical action. Additionally, through the growth process of the biofilm, the microbial composition changes from one that is primarily gram-positive and *streptococcus*-rich to a structure filled with gram-negative anaerobes in its more mature state.

The first step in biofilm development is the adsorption of host and bacterial molecules to the surface. Within minutes of a cleaning, biofilm formation begins, which can be defined as a thin coat of microbes. This layer acts like an adhesive by sticking to the surface and encouraging a conditioning film of bacteria to attach to the surface. This conditioning film directly influences the initial microbial colonization, and continues to adsorb bacteria to the tooth surface.

There are many distinct habitats most of which are bathed in ionic solutions. In order to survive bacteria must attach to one of its surfaces or risk being at the risk of air and fluid flows. Bacteria attaching to exposed smooth surfaces must be quite firmly attached to resist the flow of air and water. Any build-up of cells due to multiplication is more easily dislodged because the mass of bacteria experiences a greater shear force. This does not mean that the exposed, smooth, surfaces of teeth are devoid of attached bacteria because some species have evolved efficient adhesion mechanisms. It does mean, however, that any significant build-up is inhibited and that plaque accumulation is limited to sheltered sites such as interproximal areas, the gingival margin and fissures. Bacteria will also accumulate in defects.

Before plaque can accumulate, the surface has to be colonised by bacteria which then multiply and attract further colonisers. These "first colonisers" are known as pioneer species.

The surfaces of these cells and, in fact the surfaces of nearly all cells, are negatively charged because of the presence of proteins and other wall and cell membrane components which contain phosphate, carboxyl and other acidic groups. Furthermore, nearly all non-biological surfaces are also negatively charged. Sometimes this is due to the accumulation of organic material which adsorbs to the surface from the environment and sometimes because the surface is inherently negatively charged because of its chemistry. However, the presence of high amounts of positively charged ionic multivalent metals in the surrounding fluid, and in the biofilm fluid, causes the bacteria to be attracted to the negatively charged surface (DLVO Theory.)

As the concentration of multivalent metals continues to build in the biofilm, it reaches levels, where small changes in pH can cause the precipitation of metal salts onto the surface. These precipitates build up over time. This deposits will then cause erosion and damage to the surface.

Multivalent metals like calcium being common are often involved in biofilm production and its detrimental effects, hence a reduction in metal levels will play a key role in treating the adverse conditions on surfaces. Current treatment modalities do not take this approach, but rather depend upon mechanical removal of biofilms on teeth and other wet surfaces.

Removal of multivalent metals like calcium could be accomplished by means of calcium chelators. However, chelators are also negatively charged molecules, and are therefore repelled from the biofilm surface. Therefore to accomplish the task of getting these chelators into the plaque and close to the metals, a charge-masking, permeation-enhancing carrier allows the chelators to get to the target metal ion, e.g. calcium. The sequestration inactivating moiety may also facilitate transport of the metal ion sequestering agent through biological membranes.

Without wishing to be bound by theory, it appears that a significant role played by the biocompatible chelating agent in the present formulations is in the removal of the metals (such as copper, iron, and calcium) from the biofilm which allow easier mechanical removal of the biofilm and slows down the rebuilding of the unhealthy biofilms.

Accordingly, the chelating agent is multifunctional in the context of the present invention, insofar as the agent serves to decrease unwanted proteinase (e.g., collagenase) activity, prevent formation of mineral deposits, and/or reduce mineral deposits that have already formed, and reduce calcification, in addition to acting as a preservative and stabilizing agent. The formulation also includes an effective amount of a transport enhancer that facilitates penetration of the formulation components through cell membranes, tissues, and extracellular matrices, including the gums and other oral tissue. The "effective amount" of the transport enhancer represents a concentration that is sufficient to provide a measurable increase in penetration of one or more of the formulation components through membranes, tissues, and extracellular matrices as just described. Suitable transport enhancers include, by way of example, methylsulfonylmethane (MSM; also referred to as methyl sulfone), combinations of MSM with dimethylsulfoxide (DMSO), or a combination of MSM and, in a less preferred embodiment, DMSO, with MSM particularly preferred.

MSM is an odorless, highly water-soluble (34% w/v @ 79° F.) white crystalline compound with a melting point of 108-110° C. and a molecular weight of 94.1 g/mol. MSM serves as a multifunctional agent herein, insofar as the agent not only increases cell membrane permeability, but also acts as a "transport facilitating agent" (TFA) that aids in the transport of one or more formulation components to oral tissues. Furthermore, MSM per se provides medicative effects, and can serve as an anti-inflammatory agent as well as an analgesic. MSM also acts to improve oxidative metabolism in biological tissues, and is a source of organic sulfur, which assists in the reduction of scarring. MSM additionally possesses unique and beneficial solubilization properties, in that it is soluble in water, as noted above, but exhibits both hydrophilic and hydrophobic properties because of the presence of polar S=O groups and nonpolar methyl groups. The molecular structure of MSM also allows for hydrogen bonding with other molecules, i.e., between the oxygen atom of each S=O group and hydrogen atoms of other molecules, and for formation of van der Waal associations, i.e., between the methyl groups and nonpolar (e.g., hydrocarbyl) segments of other molecules. Ideally, the concentration of MSM in the present formulations is in the range of about 0.1 wt. % to 40 wt. %, or from about 1 wt. % to about 4, 5, 6, 7, 8, 10, 15 wt. %, and preferably between about 1.5 wt. % to 8.0 wt. %.

Other optional additives in the present formulations include secondary enhancers, i.e., one or more additional transport enhancers. For example, formulation of the invention can contain added DMSO. Since MSM is a metabolite of DMSO (i.e., DMSO is enzymatically converted to MSM), incorporating DMSO into an MSM-containing formulation of the invention will tend to gradually increase the fraction of MSM in the formulation. DMSO also serves as a free radical scavenger, thereby reducing the potential for oxidative damage. If DMSO is added as a secondary enhancer, the amount is preferably in the range of about 1.0 wt. % to 2.0 wt. % of the formulation, and the weight ratio of MSM to DMSO is typically in the range of about 1:50 to about 50:1.

Formulations

A variety of means can be used to formulate the compositions of the invention.

Techniques for formulation and administration may be found in "Remington: The Science and Practice of Pharmacy," Twentieth Edition, Lippincott Williams & Wilkins, Philadelphia, Pa. (1995). For human or animal administration, preparations should meet sterility, pyrogenicity, general safety and purity standards comparable to those required by the FDA. Administration of the pharmaceutical formulation can be performed in a variety of ways, as described herein.

Other possible additives for incorporation into the formulations that are at least partially aqueous include, without limitation, thickeners, isotonic agents, buffering agents, and preservatives, providing that any such excipients do not interact in an adverse manner with any of the formulation's other components. It should also be noted that preservatives are not generally necessarily in light of the fact that the selected chelating agent itself serves as a preservative. Suitable thickeners will be known to those of ordinary skill in the art of formulation, and include, by way of example, cellulosic polymers such as methylcellulose (MC), hydroxyethylcellulose (HEC), hydroxypropylcellulose (HPC), hydroxypropyl-methylcellulose (HPMC), and sodium carboxymethylcellulose (NaCMC), and other swellable hydrophilic polymers such as polyvinyl alcohol (PVA), hyaluronic acid or a salt thereof (e.g., sodium hyaluronate), and cross-linked acrylic acid polymers commonly referred to as "carbomers" (and available from B.F. Goodrich as Carbopol® polymers). Various organic gums such as but not limited to Xanthan gum and Konjac gum. The preferred amount of any thickener is such that a viscosity above 10,000 cps is provided, as a gel having a viscosity above this FIGURE generally considered optimal for both comfort and retention of the formulation on the oral tissues. Any suitable isotonic agents and buffering agents commonly used in oral formulations may be used, providing the pH of the formulation is maintained in the range of about 4.5 to about 9.0, preferably in the range of about 6.8 to about 7.8, and optimally at a pH of about 7.4.

The formulations of the invention also include a pharmaceutically acceptable carrier, which will depend on the particular type of formulation. For example, the formulations of the invention can be provided as a solution, suspension, paste or gel, in which case the carrier is at least partially aqueous. The formulations may also be ointments, in which case the pharmaceutically acceptable carrier is composed of an ointment base. Preferred ointment bases herein have a melting or softening point close to body temperature, and any ointment bases commonly used in oral preparations may be advantageously employed. Common ointment bases include petrolatum and mixtures of petrolatum and mineral oil.

The pharmaceutical formulation may be a solid, semi-solid or liquid, such as, for example, a liquid, a cream, a suspension, an emulsion, beads, a powder, or the like, preferably in unit dosage form suitable for single administration of a precise dosage. Suitable pharmaceutical formulations and dosage forms may be prepared using conventional methods known to those in the field of pharmaceutical formulation and described in the pertinent texts and literature, e.g., in Remington: The Science and Practice of Pharmacy, cited previously herein.

The formulations of the invention may also be prepared as a hydrogel, dispersion, or colloidal suspension. Hydrogels are formed by incorporation of a swellable, gel-forming polymer such as those set forth above as suitable thickening agents (i.e., MC, HEC, HPC, HPMC, NaCMC, PVA, or hyaluronic acid or a salt thereof, e.g., sodium hyaluronate), except that a formulation referred to in the art as a "hydrogel" typically has a higher viscosity than a formulation referred to as a "thickened" solution or suspension. In contrast to such preformed hydrogels, a formulation may also be prepared so as to form a hydrogel in situ following application into the oral cavity. Such gels are liquid at room temperature but gel at higher temperatures (and thus termed "thermoreversible" hydrogels), such as when placed in contact with body fluids. Biocompatible polymers that impart this property include acrylic acid polymers and copolymers, N-isopropylacrylamide derivatives, and ABA block copolymers of ethylene oxide and propylene oxide (conventionally referred to as "poloxamers" and available under the Pluronic® trade name from BASF-Wyandotte). The formulations can also be prepared in the form of a dispersion or colloidal suspension. Preferred dispersions are liposomal, in which case the formulation is enclosed within "liposomes," microscopic vesicles composed of alternating aqueous compartments and lipid bilayers. Colloidal suspensions are generally formed from microparticles, i.e., from microspheres, nanospheres, microcapsules, or nanocapsules, wherein microspheres and nanospheres are generally monolithic particles of a polymer matrix in which the formulation is trapped, adsorbed, or otherwise contained, while with microcapsules and nanocapsules, the formulation is actually encapsulated. The upper limit for the size for these microparticles is about 5µ to about 10µ.

The formulations may also be incorporated into a sterile insert that provides for controlled release of the formulation over an extended time period, generally in the range of about 12 hours to 60 days, and possibly up to 12 months or more, following implantation of the insert into any tissue. One type of insert is an implant in the form of a monolithic polymer matrix that gradually releases the formulation to the oral tissues through diffusion and/or matrix degradation. With such an insert, it is preferred that the polymer be completely soluble and or biodegradable (i.e., physically or enzymatically eroded in the tissues) so that removal of the insert is unnecessary. These types of inserts are well known in the art, and are typically composed of a water-swellable, gel-forming polymer such as collagen, polyvinyl alcohol, or a cellulosic polymer. Another type of insert that can be used to deliver the present formulation is a diffusional implant in which the formulation is contained in a central reservoir enclosed within a permeable polymer membrane that allows for gradual diffusion of the formulation out of the implant. Osmotic inserts may also be used, i.e., implants in which the formulation is released as a result of an increase in osmotic pressure within the implant following application to the oral tissue and subsequent absorption.

The chelating agent may be administered, if desired, in the form of a salt, ester, crystalline form, hydrate, or the like, provided it is pharmaceutically acceptable. Salts, esters, etc. may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992).

The amount of chelating agent administered will depend on a number of factors and will vary from subject to subject and depend on the particular chelating agent, the particular disorder or condition being treated, the severity of the symptoms, the subject's age, weight and general condition, and the judgment of the prescribing physician. The term "dosage form" denotes any form of a pharmaceutical composition that contains an amount of chelating agent and transport enhancer sufficient to achieve a therapeutic effect with a single administration or multiple administrations. The frequency of administration that will provide the most effective results in an efficient manner without overdosing will vary with the characteristics of the particular active agent, including both its pharmacological characteristics and its physical characteristics, such as hydrophilicity.

The formulations may also include conventional additives such as opacifiers, flavoring agents, antioxidants, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from the methyl and propyl esters of p-hydroxybenzoic acid (i.e., methyl and propyl paraben), sodium benzoate, sorbic acid, imidurea, and combinations thereof.

The active formulation of the invention can be formulated in combination with one or more pharmaceutically-acceptable anti-microbial agents. In this regard, combinations of different antimicrobial agents may be tailored to target different (or the same) microorganisms that contribute towards morbidity and mortality. The pharmaceutically acceptable anti-microbial agents of the present invention are suitable for internal administration to an animal, for example, a human. However, if the formulation is to be used in industrial sterilizing, sterilizing chemicals such as detergents, disinfectants, and ammonium-based chemicals (e.g. quaternary ammonium compounds such as QUATAL) can be used in combination with, or prior to or after the treatment with the formulation. Such sterilizing chemicals are typically used in the art for sterilizing industrial work surfaces (e.g. in food processing, or hospital environments), and are not suitable for administration to an animal.

The invention further contemplates preparations, formulations, coatings, films, oils, and composite materials that contain the formulation of the invention. Such materials are useful in many varied industrial and medical applications. Industrial applications include marine applications such as fouling-release treatments for surfaces of ships and boats such as the hull, offshore marine structures such as oil rigs, sea water conduit systems for seaside plants, buoys, heat exchangers, cooling towers, desalination equipment, filtration membranes, docks, aquatic zoo and aquarium and other structures which may all experience some degree of fouling when continually exposed to fresh or salt water. Medical applications include use as treatments for devices, including implantable devices, such as tubing, catheters, stents, vascular implants, cardiac regulation devices, and other devices that come into contact with body fluids.

The formulation can be incorporated into any cleaning agent. If EDTA or some other chelator is already present in the cleaning agent then only the transport enhancer (e.g., MSM) need to be included. If not, a chelator and a transport enhancer (MSM/EDTA) are added.

Methods of using the formulation of the invention are also included. The formulation can be used as a cleaning agent for specific medical devices such as a contact lens. Devices such as tubes (e.g., intra-venous tubing) and catheters may be treated with the formulation by rinsing the interior surface for a period of time and a number of applications that are found suitable for removal of a desired level of biofilm. Tubes intended for industrial use can also be rinsed or otherwise treated with the formulation for removal of biofilm, or prevention of formation of biofilm.

The formulation can be used as a cleaning agent generally as a wipe. A wipe according to the invention may comprise a fabric suitable for wiping a surface wherein the wipe is pre-soaked with a lotion containing the formulation. Alternately, the formulation can be applied directly (e.g., by spraying, pouring, etc.) followed by wiping.

In some embodiments, the formulation may be applied to a surface susceptible to biofilm formation. The formulations can be applied to coat or form surfaces of articles used in industrial, marine, and medical applications.

The treatment regimen will depend on a number of factors that may readily be determined, such as severity of the condition and responsiveness of the microbial infection to be treated, but will normally be one or more treatments per day, with a course of treatment lasting from a day or several days to several months, or until a significant reduction of biofilm is achieved.

The compositions of the invention may further include additional drugs or excipients as appropriate for the indication. In one aspect of the embodiment, the pharmaceutical composition further comprises a therapeutically effective amount of at least one antimicrobial agent. In a more specific aspect, the antimicrobial agent is an antibiotic.

In another embodiment, the present invention provides a method for inhibiting formation of a biofilm on a device, the method comprising contacting the bacteria with an effective amount of a formulation comprising a transport enhancer (such as MSM) and a chelating agent (such as EDTA), whereby formation of a biofilm on the device is inhibited. The composition may be, for example, a spray, lotion, solution, gel, cream, ointment, surgical rinse, or dental rinse. In another embodiment, the composition may be a device-soaking solution, a personal cleaning composition, or a hard surface cleaning composition. In such compositions, the proportion of the EDTA to MSM is in the range of about 1:100-100:1, and the percentages of EDTA and MSM in the composition are in the ranges of about 0.1% to 15% and about 0.1% to 40% by weight, respectively.

In another embodiment, the present invention provides a topical pharmaceutical composition for inhibiting formation of a biofilm on or within a mammal, comprising an effective amount of a formulation comprising a transport enhancer (such as MSM) and a chelating agent (such as EDTA, tetrasodium salt of iminodisuccinic acid, poly-aspartic acid and/or salts thereof, or tetra sodium salts of L-glutamic acid N,N-diacetic acid (GLDA), and at least one pharmaceutically acceptable carrier.

In a further embodiment, the present invention provides a surgical rinse for inhibiting formation of a biofilm comprising bacteria, wherein the surgical rinse comprises an effective amount of a formulation comprising a transport enhancer (such as MSM) and a chelating agent (such as EDTA). In one embodiment, the surgical rinse may be, for example, a buffered saline solution or a Ringer's solution. A surgical rinse of the present invention may be applied before, during, or after surgery and may be aspirated from the surgical area or left on the surgical area to inhibit biofilm formation In yet another embodiment, the present invention provides a method for inhibiting formation of a biofilm comprising bacteria, the method comprising contacting the bacteria with an effective amount of a formulation comprising a transport enhancer (such as MSM) and a chelating agent (such as EDTA), wherein the bacteria are selected from the group consisting of *Acidothennus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtheriae, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Fingoldia magna, Geobacillus kaustophilus, Geobacillus thermodenitrificans, Janibacter* sp., *Kineococcus radiotolerans, Lactobacillus fennentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides* sp., *Nocardia farcinica, Oceanobacillus iheyensis, Pelotomaculum thermopropionicum, Rhodococcus* sp., *Saccharopolyspora erythraea*, coagulase-negative *Staphylococcus* species, *Staphylococcus aureus*, methicillin resistant

*Staphylococcus aureus* (MRSA), *Staphylococcus epidermidis*, methicillin resistant *Staphylococcus epidermidis* (MRSE), *Streptococcus agalactiae, Streptococcus gordonii, Streptococcus mitis, Streptococcus oxalis, Streptococcus pneumoniae, Streptococcus sanguinis, Streptococcus suis, Streptomyces avermitilis, Streptomyces coelicolor, Thermoanaerobacter ethanolicus, Thermoanaerobacter tengcongensis*, and combinations thereof, whereby formation of the biofilm is inhibited.

A further embodiment of the present invention provides bandages, sponges or gauzes impregnated with a safe and effective amount of a formulation comprising a transport enhancer (such as MSM) and a chelating agent (such as EDTA), wherein the bandage, sponge or gauze inhibits the formation of a biofilm on the skin. In one embodiment, the bandage, sponge or gauze is suitable for use in patients with cuts, burns, turf burns, abrasions, lacerations, puncture wounds, regions of bacterial infection such as boils and pustules, and the like.

Yet another embodiment of the present invention provides a personal cleansing formulation comprising a transport enhancer (such as MSM) and a chelating agent including but not limited to, EDTA and salts thereof, or tetrasodium salt of iminodisuccinic acid, or salts of poly-aspartic acid, or tetra sodium salts of L-glutamic acid N,N-diacetic acid (GLDA) .), wherein the personal cleansing composition inhibits formation of a biofilm on the skin. Suitable personal cleansing compositions include, but are not limited to, surgical scrubs, shower gels, body washes, soaps, deodorants, and the like. In another embodiment of the invention, the personal cleansing composition is applied as a part of a personal hygiene routine. Personal cleansing compositions of the present invention are suitable for use by a variety of individuals, including, for example, people recovering from Staph infections, athletes using team locker rooms, and healthcare professionals.

A further embodiment of the present invention provides a hard surface cleaning formulation comprising a transport enhancer (such as MSM) and a chelating agent (such as EDTA), wherein the composition inhibits formation of a biofilm on a hard surface. The present hard surface cleaning composition has a variety of useful applications, including use in industrial applications as well as medical, veterinary, or livestock environments. For example, hard surface cleaners of the present invention are useful in the cleaning and treating of pipeline systems, cooling water systems in power plants, refineries, chemical plants, air conditioning systems, storage tanks, trays, containers, walls, floors, countertops, locker room floors, benches, lockers, showers, bathrooms, toilets, water filtration units, and the like, as part of a standard cleaning routine.

A further embodiment of the present invention provides a dental rinse for inhibiting formation of a biofilm, the dental rinse comprising a formulation comprising a transport enhancer (such as MSM) and a chelating agent (such as EDTA).

For topical administration to the epidermis, a formulation comprising a transport enhancer (such as MSM) and a chelating agent (such as EDTA) of the present invention may be formulated in an ointment, cream, or lotion, or as a transdermal patch. Ointments and creams, may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges comprising a formulation comprising a transport enhancer (such as MSM) and a chelating agent (such as EDTA) in a flavored base, usually sucrose and acacia or tragacanth; pastilles comprising the active ingredients in an inert base such as gelatin and glycerin or sucrose and acacia; and mouth washes comprising the active ingredients in a suitable liquid carrier. For topical administration to the eye, the formulation comprising a transport enhancer (such as MSM) and a chelating agent (such as EDTA) can be made up in solution or suspension in a suitable sterile aqueous or non-aqueous vehicle. Additives such as buffers (e.g. sodium metabisulphite or disodium edeate) and thickening agents such as hypromellose can also be included.

For intra-nasal administration, a formulation comprising a transport enhancer (such as MSM) and a chelating agent (such as EDTA) of the present invention can be provide in a liquid spray or dispersible powder or in the form of drops. Drops may be formulated with an aqueous or non-aqueous base also comprising one or more dispersing agents, solubilizing agents, or suspending agents. Liquid sprays are conveniently delivered from pressurized packs.

For administration by inhalation, a formulation comprising a transport enhancer (such as MSM) and a chelating agent (such as EDTA) of the present invention can be delivered by insufflator, nebulizer or a pressurized pack or other convenient means of delivering the aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

In another embodiment of the present invention, wound dressings including but not limited to sponges or gauzes can be impregnated with a formulation comprising a transport enhancer (such as MSM) and a chelating agent (such as EDTA) to prevent or inhibit bacterial or fungal attachment and reduce the risk of wound infections. Similarly, catheter shields as well as other materials used to cover a catheter insertion sites can be coated or impregnated with a formulation comprising a transport enhancer (such as MSM) and a chelating agent (such as EDTA) to inhibit bacterial or fungal biofilm attachment thereto. Adhesive drapes used to prevent wound infection during high risk surgeries can be impregnated with the isolated protein or active fragment or variant thereof as well. Additional medical devices which can be coated with a formulation comprising a transport enhancer (such as MSM) and a chelating agent (such as EDTA) include, but are not limited, central venous catheters, intravascular catheters, urinary catheters, Hickman catheters, peritoneal dialysis catheters, endrotracheal catheters, mechanical heart valves, cardiac pacemakers, arteriovenous shunts, schleral buckles, prosthetic joints, tympanostomy tubes, tracheostomy tubes, voice prosthetics, penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Exemplary solutions for impregnating gauzes or sponges, catheter shields and adhesive drapes or coating catheter shields and other medical devices include, but are not limited to, phosphate buffered saline (pH approximately 7.5) and bicarbonate buffer (pH approximately 9.0).

In yet another embodiment, a formulation comprising a transport enhancer (such as MSM) and a chelating agent (such as EDTA) can be incorporated in a liquid disinfecting solution. Such solutions may further comprise antimicrobials or antifungals such as alcohol, providone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok connectors, needleless connectors and hubs as well as other implantable devices. These solutions can also be used to coat or disinfect surgical instruments including, but not limited to, clamps, forceps, scissors, skin hooks, tubing, needles, retractors, scalers, drills, chisels, rasps and saws.

EXAMPLES

The following examples are put forth so as to provide those skilled in the art with a complete invention and description of how to make and use embodiments in accordance with the invention, and are not intended to limit the scope of what the inventors regard as their discovery. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Reduction of Plaque Development after Single Brushing

Toothpaste was prepared comprising EDTA (tetrasodium salt) and MSM, which were purchased from Sigma. Control was a leading "anti-plaque" toothpaste available in the market.

| Treatment | Reduction in Plaque Index |
| --- | --- |
| Control toothpaste | 1.11 |
| 5.4% MSM/2.6% EDTA tooth gel | 2.29 |
| 5.0% MSM/2.0% sodium citrate gel | 1.87 |
| 5.0% MSM/2.0% sodium phytate gel | 1.73 |

The MSM/EDTA toothpaste showed 106% greater reduction in plaque. This showed a high degree of statistical significance.

Example 2

Reduction of Plaque Development after Repeated Brushings

Toothpaste was prepared comprising EDTA (tetrasodium salt) and MSM, which were purchased from Sigma. Control was a leading "anti-plaque" toothpaste available in the market. Loe Sillness dental plaque index was measured on subjects after 2 weeks of twice daily brushing, after an initial prophylaxis.

| Treatment | Plaque Index |
| --- | --- |
| Control toothpaste | 1.89 |
| 5.4% MSM/2.6% EDTA tooth gel | 0.13 |
| 5.0% MSM/2.0% sodium citrate gel | 0.95 |
| 5.0% MSM/2.0% sodium phytate gel | 1.18 |

The MSM+chelator results compared to control showed extremely high statistical significance.

Example 3

96-Well Microtiter Plate Biofilm Cell Detachment Assay

The wells of a 96-well microtiter plate (Falcon no. 353072) were filled with 100 µl of medium containing $10^2$ to $10^4$ CFU of bacteria and incubated at 37° C. in 10% $CO_2$ for 20 hours. Ten µl of enzyme solution [1 mg/ml in phosphate buffered saline (PBS)], or 10 µl of PBS in the case of controls, was added to each well and the plates were incubated for an additional 6 hours. The wells were washed extensively under running tap water and the bacteria remaining attached to the surface were stained with crystal violet, rewashed, and destained with ethanol in accordance with procedures described by Kachlany et al. Mol. Microbiol. 2001 40:542-554). The optical density (O.D.) of the ethanol-dye solution was measured in a BioRad Benchmark microtiter plate reader set to 590 nm.

Example 4

Effect of the Formulation on Underarm Polymicrobial Biofilms that Lead to Underarm Body Odor A relatively benign polymicrobial infection called *Trichomichosis axillaris* infests the underarm skin and hair of a large number of people. This infestation produces unsightly deposits on axillary hair as shown in the FIGURE below. This infestation also leads to an intensely unpleasant body odor.

The standard treatment for this condition is to shave the affected area, and then to apply antimicrobial creams and lotions, for example benzoyl peroxide or erythromycin cream—this treatment modality often results in irritation and contact dermatitis. The average time for resolution of the disease has been characterized as 3 weeks (Kim Comparative Study of Benzoyl Peroxide Versus Erythromycin in *Trichomycosis Axillaris* and Pubis, *Korean J Med Mycol.* 2005 June; 10(2):70-75.). A gel of MSM/EDTA of the formulation was applied once a day in five patients with *Trichomichosis axillaris*. The infection in each case disappeared within three days. At the same time, all underarm malodor in the patients resolved, and no patient showed any irritation or contact dermatitis. A picture of the before and after of one patient is shown in FIGS. 1a-1b.

Example 4

Effect of the Formulation on Cat Bite Infections 20 to 80% of all cat bite wounds get infected with a polymicrobial infection within 24 hours, with the first signs appearing after 12 hours. Treatment with traditional antimicrobials is often prolonged, and it takes weeks to months to heal the badly infected wounds. The infection occurs because remnants of cat dental plaque get left behind in the wound and cannot be cleaned by traditional wound cleaning methods. (A. Freshwater, Why Your Housecat's *Trite* Little Bite Could Cause You Quite a Fright: A Study of Domestic Felines on the Occurrence and Antibiotic Susceptibility of *Pasteurella multocida*, Journal compilation 2008 Blackwell Verlag Zoonoses Public Health. 55 (2008) 507-513; J. Sillery; et al., *Pasteurella multocida* Peritonitis: Another Risk of Animal-Assisted Therapy, Source: *Infection Control and Hospital Epidemiology*, Vol. 25, No. 1 (January 2004), pp. 5-6, Published by: The University of Chicago Press on behalf of The Society for Healthcare Epidemiology of America; Itzhak Brook, et al, Animal bite-associated infections: microbiology and treatment, *Expert Review of Anti-Infective therapy*, 9.2 (February 2011): p 215). Over a hundred cat bite wounds were treated with one of a lotion or a gel comprising of MSM and EDTA within an hour of injury. None of the wounds were infected, and all wounds healed within three days.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. An antimicrobial formulation, comprising:
a chelating agent or salts thereof;
a transport enhancer, wherein the transport enhancer is MSM; and
an acceptable vehicle or base for such composition;
wherein the combination of the chelating agent and the transport enhancer is present in a proportion effective to bring about a significant reduction in bacterial and/or fungal biofilm on a surface to which it is applied, and wherein the percentage of chelator is about 0.1% to 15% and the percentage of transport in the composition is about 0.1% to 40% by weight, respectively.

2. The formulation of claim 1, wherein the proportion of the chelator to MSM is in the range of about 10:1-1:20.

3. The formulation of claim 1, wherein the composition comprises a formulation selected from solid, liquid, inhalant, spray, lotion, solution, gel, cream, ointment, surgical rinse, or dental rinse.

4. The formulation of claim 1, wherein the chelating agent is selected from ethylenediamine tetraacetic acid (EDTA), ethylene glycol tetraacetic acid (EGTA), cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccinic acid (DMSA), aminotrimethylene phosphonic acid (ArPA), citric acid, acetic acid and acceptable salts thereof, and any combinations thereof.

5. The formulation of claim 1, wherein the chelating agent is selected from:
(a) phosphates, pyrophosphates, tripolyphosphates, or hexametaphosphates;
(b) a chelating antibiotic, chloroquine or tetracycline;
(c) a nitrogen-containing chelating agent containing two or more chelating nitrogen atoms within an imino group or in an aromatic ring, diimines, or 2,2'-bipyridines;
(d) a polyamine selected from cyclam (1,4,7,11-tetraazacyclotetradecane), N—($C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), deferoxamine (N'-{5-[Acetyl(hydroxy)amino] pentyl}-N-[5-({4-[(5-aminopentyl)(hydroxy)amino]-4-oxobutanoyl}amino)pentyl]-N-hydroxysuccinamide, or N'-[5-(Acetyl-hydroxy-amino)pentyl]-N-[5-[3-(5-aminopentyl-hydroxy-carbamoyl) propanoylamino] pentyl]-N-hydroxy-butane diamide), desferrioxamine B, desferoxamine B, DFO-B, DFOA, DFB, desferal, deferiprone, pyridoxal isonicotinoyl hydrazone (PIH), salicylaldehyde isonicotinoyl hydrazone (SIH), and ethane-1,2-bis(N-1-amino-3-ethylbutyl-3-thiol);
(e) a EDTA-4-aminoquinoline conjugate selected from ([2-(Bis-ethoxycarbonylmethyl-amino)-ethyl]-{[2-(7-chloro-quinolin-4-ylamino)-ethylcarbamoyl]-methyl}-amino)-acetic acid ethyl ester, ([2-(Bis-ethoxycarbonylmethyl-amino)-propyl]-{[2-(7-chloro-quinolin-4-ylamino)-ethylcarbamoyl]-methyl}-amino)-acetic acid ethyl ester, ([3-(Bis-ethoxycarbonylmethyl-amino)-propyl]-{[2-(7-chloro-quinolin-4-ylamino)-ethylcarbamoyl]-methyl}-amino)-acetic acid ethyl ester, ([4-(Bis-ethoxycarbonylmethyl-amino)-butyl]-{[2-(7-chloro-quinolin-4-ylamino)-ethylcarbamoyl]-methyl}-amino)-acetic acid ethyl ester, ([2-(Bis-ethoxymethyl-amino)-ethyl]-{[2-(7-chloro-quinolin-4-ylamino)-ethylcarbamoyl]-methyl}-amino)-acetic acid ethyl ester, ([2-(Bis-ethoxymethyl-amino)-propyl]-{[2-(7-chloro-quinolin-4-ylamino)-ethylcarbamoyl]-methyl}-amino)-acetic acid ethyl ester, ([3-(Bis-ethoxymethyl-amino)-propyl]-{[2-(7-chloro-quinolin-4-ylamino)-ethylcarbamoyl]-methyl}-amino)-acetic acid ethyl ester, ([4-(Bis-ethoxymethyl-amino)-butyl]-{[2-(7-chloro-quinolin-4-ylamino)-ethylcarbamoyl]-methyl}-amino)-acetic acid ethyl ester;
(f) a tetrasodium salt of iminodisuccinic acid;
(g) poly-asparatic acid or a salt thereof;
(h) a tetra sodium salt of L-glutamic acid N,N-diacetic acid; and
(i) a natural chelator selected from citric acid, phytic acid, lactic acid, acetic acid and their salts and curcumin.

6. The formulation of claim 1, further comprising an antibiotic agent wherein the antibiotic is antibacterial or antifungal.

7. The formulation of claim 1, wherein the formulation is for oral administration, parenteral administration, topical administration, intra-nasal administration, timed release, an ointment, a cream, or a lotion.

8. A method for inhibiting a biofilm associated bacterial infection comprising administering the formulation of claim 1 in combination with or prior to administration of an antibiotic.

9. A medical device coated with the formulation of claim 1, wherein the medical device is selected from the group consisting of an implantable device, a central venous catheter, an intravascular catheter, an urinary catheter, a Hickman catheter, a peritoneal dialysis catheter, an endrotracheal catheter, a mechanical heart valve, a cardiac pacemaker, an arteriovenous shunt, a schleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a surgical instrument and a vascular graft.

10. A wound dressing impregnated with the formulation of claim 1.

11. A transdermal patch comprising the formulation of claim 1.

12. A method for promoting detachment of bacterial or fungal cells from a biofilm comprising contacting bacterial cells with the formulation of claim 1.

13. A method of inhibiting infection on a medical device or surgical instrument by bacteria or fungi comprising contacting the medical device or surgical instrument with the formulation of claim 1.

14. The method of claim 13 further comprising: (a) coating the medical device or surgical instrument with the formulation of claim 1 or (b) bathing the medical device or surgical instrument in a solution comprising the formulation of claim 1.

15. A method of inhibiting or treating bacterial or fungal infections comprising administering a pharmaceutically acceptable composition comprising the formulation of claim 1 wherein the bacteria is selected from the group consisting of a gram-positive bacteria, *Acidothermus cellulyticus, Actinomyces odontolyticus, Alkaliphilus metalliredigens, Alkaliphilus oremlandii, Arthrobacter aurescens, Bacillus amyloliquefaciens, Bacillus clausii, Bacillus halodurans, Bacillus licheniformis, Bacillus pumilus, Bacillus subtilis, Bifidobacterium adolescentis, Bifidiobacterium longum, Caldicellulosiruptor saccharolyticus, Carboxydothermus hydrogenoformans, Clostridium acetobutylicum, Clostridium beijerinckii, Clostridium botulinum, Clostridium cellulolyticum, Clostridium difficile, Clostridium kluyveri, Clostridium leptum, Clostridium novyi, Clostridium perfringens, Clostridium tetani, Clostridium thermocellum, Corynebacterium diphtheriae, Corynebacterium efficiens, Corynebacterium glutamicum, Corynebacterium jeikeium, Corynebacterium urealyticum, Desulfitobacterium hafniense, Desulfotomaculum reducens, Eubacterium ventriosum, Exiguobacterium sibiricum, Fingoldia magna, Geobacillus kaustophilus, Geobacillus thennodenitrificans, Janibacter* sp., *Kineococcus radiotolerans, Lactobacillus fermentum, Listeria monocytogenes, Listeria innocua, Listeria welshimeri, Moorella thermoacetica, Mycobacterium avium, Mycobacterium bovis, Mycobacterium gilvum, Mycobacterium leprae, Mycobacterium paratuberculosis, Mycobacterium smegmatis, Mycobacterium tuberculosis, Mycobacterium ulcerans, Mycobacterium vanbaalenii, Nocardioides* sp., *Nocardia farcinica, Oceanobacillus iheyensis, Pelotomaculum thermopropionicum, Rhodococcus* sp., *Saccharopolyspora erythraea*, coagulase-negative *Staphylococcus* species, *Staphylococcus aureus*, methicillin resistant *Staphylococcus aureus* (MRSA), *Staphylococcus epidermidis*, methicillin resistant *Staphylococcus epidermidis* (MRSE), *Streptococcus agalactiae, Streptococcus gordonii, Streptococcus mitis, Streptococcus oralis, Streptococcus pneumoniae, Streptococcus sanguinis, Streptococcus suis, Streptomyces avermitilis, Streptomyces coelicolor, Thennoanaerobacter ethanolicus, Thermoanaerobacter tengcongensis*, and combinations thereof.

16. A bandage impregnated with a safe and effective amount of the formulation of claim 1, wherein the bandage inhibits the formation of a biofilm on the skin.

17. A personal cleansing composition comprising an effective amount of the formulation of claim 1, wherein the personal cleansing composition inhibits formation of a biofilm on the skin.

18. A hard surface cleaning composition comprising an effective amount of the formulation of claim 1, wherein the composition inhibits formation of a biofilm on the hard surface and wherein the hard surface cleaning composition comprises:
 about 0.4-15% of chelator;
 about 0.5-30% of MSM;
 one or more thickening and gelling agents;
 10-99% water; and
 optionally contains surfactants, detergents and/or soaps.

19. A dental rinse for inhibiting formation of a biofilm, the dental rinse comprising an effective amount of the formulation of claim 1.

20. The hard surface cleaning composition of claim 18, comprising:
 about 1-5% of chelator;
 about 1-10% of MSM;
 0.1-6% of one or more thickening agents; and
 80-97% water.

* * * * *